US00PP15399P3

(12) United States Plant Patent
Zaiger et al.

(10) Patent No.: US PP15,399 P3
(45) Date of Patent: Dec. 7, 2004

(54) CHERRY TREE NAMED 'ROYAL KAY'

(50) Latin Name: *Prunus avium*
Varietal Denomination: Royal Kay

(76) Inventors: Gary Neil Zaiger, 1907 Elm Ave., Modesto, CA (US) 95358; Leith Marie Gardner, 1207 Grimes Ave., Modesto, CA (US) 95358; Grant Gene Zaiger, 4005 California Ave., Modesto, CA (US) 95358

( * ) Notice: Subject to any disclaimer, the term of this patent is extended or adjusted under 35 U.S.C. 154(b) by 93 days.

(21) Appl. No.: 10/302,701

(22) Filed: Nov. 25, 2002

(65) Prior Publication Data

US 2004/0103463 P1 May 27, 2004

(51) Int. Cl.[7] ..... A01H 5/00
(52) U.S. Cl. ..... Plt./181

(58) Field of Search ..... Plt./181

*Primary Examiner*—Anne Marie Grunberg

(57) ABSTRACT

A new and distinct variety of cherry tree (*Prunus avium*). The following features of the tree and its fruit are characterized with the tree budded on 'Mahaleb' Rootstock (non-patented), grown on Handford sandy loam soil with Storie Index rating 95, in USDA Hardiness Zone 9, near Modesto, Calif., with standard commercial fruit growing practices such as pruning, thinning, spraying, irrigation and fertilization. Its novelty consist of the following combination of desirable features:

1. Vigorous, upright tree growth.
2. Fruit maturing in the early season.
3. Fruit with attractive red skin color.
4. Heavy and regular production of large size fruit.
5. Fruit with very good flavor and eating quality.
6. Fruit with good handling and storage quality.

1 Drawing Sheet

BACKGROUND OF THE VARIETY

1. Field of the Invention

In the field of plant genetics, we conduct an extensive and continuing plant-breeding program including the organization and asexual reproduction of orchard trees, and of which plums, peaches, nectarines, apricots, cherries and interspecifics are exemplary. It was against this background of our activities that the present variety of cherry tree was originated and asexually reproduced by us in our experimental orchard located near Modesto, Stanislaus County, Calif.

2. Prior Varieties

Among the existing varieties of cherry trees, which are known to us, and mentioned herein, are 'Stella' Cherry (non-patented) and 'Early Burlat' Cherry (non-patented).

STATEMENT REGARDING FEDERALLY SPONSORED RESEARCH AND DEVELOPMENT

Not applicable.

ORIGIN OF THE VARIETY

The present new variety of cherry tree (*Prunus avium*) was developed by us in our experimental orchard located near Modesto, Calif. The new cherry tree was selected in 1992 from a group of open pollinated seedlings grown from seed of a selected seedling with the field identification number 13HA431. The seedling cherry tree (13HA431) originated as a third generation seedling from open pollinated seed of 'Stella' Cherry (non-patented) and was selected to be used as a parent in our cherry breeding program. We grew a large number of these open pollinated seedlings on their own root under careful observation and selected the present variety for asexual reproduction due to it's heavy fruit production, early maturity, and good fruit quality.

ASEXUAL REPRODUCTION OF THE VARIETY

Asexual reproduction of the new and distinct variety of cherry tree was by budding to 'Mahaleb' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new variety of cherry tree is of large size, vigorous, upright growth and a regular bearer of large fruit with medium firmness, very good flavor and eating quality. The fruit is further characterized by its attractive red skin color and early fruit maturity. In comparison to the standard commercial cherry variety 'Early Burlat' (non-patented), the new variety blooms approximately 7 days earlier and the fruit is approximately 3 days earlier in maturity. In comparison to 'Stella' Cherry (non-patented), the new variety blooms approximately 7 days earlier and the fruit matures approximately 25 days earlier. In comparison to its parent plant, the instant plant ripens earlier.

PHOTOGRAPH OF THE VARIETY

The accompanying color photographic illustration shows typical specimens of the foliage and fruit of the present new cherry variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of cherry tree, 7 years of age, its flowers, foliage and fruit, as based on observations of specimens grown near Modesto, Calif., with color in accordance with Munsell Book of Color.

Tree:

*Size.*—Large. Tree pruned to 4 to 5 meters in height for economical harvesting of fruit.

*Vigor.*—Vigorous. Tree growth reaching 1 to 2 meters the first growing season. Growth rate varies with soil type and depth, cultural practices and climatic conditions.

*Form.*—Upright. During the first and second growing seasons scaffolds are selected and tied down to increase crotch angle and help spread tree to desired width of 3 to 4 meters.

*Branching habit.*—Upright. Crotch angle approximately 40° when juvenile, upon maturity the weight of the fruit tends to increase the branch angles.

*Productivity.*—Very productive. Produces adequate fruit set annually.

*Bearer.*—Regular. Adequate fruit set for three consecutive years.

*Fertility.*—Self sterile, pollinator required.

*Density.*—Medium dense. Usually pruned to form open vase shape to enhance health of fruit spurs and fruit color throughout the tree.

*Hardiness.*—Hardy. Tree grown in USDA Hardiness Zone 9. Winter chilling requirement is approximately 750 hours at or below 45° F.

Trunk:

*Size.*—Large. Measured 20.3 cm in circumference at 25.4 cm above ground on a 7 year old tree. Varies with soil type, climatic conditions and cultural practices.

*Stocky.*—Medium stocky.

*Texture.*—Medium rough, increases slightly with age of tree.

*Color.*—Varies from 5Y 6/2 to 7.5Y 6/2.

Branches:

*Size.*—Medium. Average circumference 12.1 cm at 1.2 meters above ground.

*Surface texture.*—Smooth on new growth, becomes medium rough on mature growth.

*Lenticels.*—Numerous. Average of 35 in a 25.8 square cm section. Average length 3.1 mm, increases in size as branches grow larger. Average width 1.6 mm. Color — 5YR 5/8.

*Color.*—New growth varies from 5Y 4/6 to 5Y 5/4. Old growth 7.5R 5/2, varies with age of growth.

Leaves:

*Size.*—Large. Average length 126.1 mm. Average width 60.9 mm.

*Form.*—Varies between ovate and lanceolate.

*Apex.*—Acuminate.

*Base.*—Cuneate.

*Margin.*—Serrate.

*Thickness.*—Medium.

*Surface texture.*—Upper surface relatively smooth, slight indentation over leaf veins, glabrous. Lower surface relatively smooth, slight ridges created by midrib and pinnate venation, glabrous.

*Petiole.*—Average length 38.1 mm. Average width 1.6 mm. Grooved longitudinally. Color of upper surface varies from 5R 2/4 to 5R 2/6. Color of lower surface varies from 2.5GY 5/6 to 2.5GY 5/8.

*Glands.*—Reniform. Large size. Number varies from 1 to 2. Average number 2. Average length 1.5 mm. Average width 1.3 mm. Located primarily on the upper portion of the petiole. Color varies from 2.5GY 8/4 to 7.5R 3/8 when exposed to the sun.

*Color.*—Upper surface varies from 5GY 3/4 to 5GY 4/4. Lower surface varies from 2.5GY 4/4 to 2.5GY 5/4.

*Midvein.*—Color varies from 5Y 5/6 to 5Y 6/6.

Flower buds:

*Size.*—Large. Average length 15.5 mm. Average diameter 6.9 mm.

*Hardiness.*—Hardy in all stone fruit growing areas in California.

*Form.*—Plump, conical.

*Pedicel.*—Average length 25.4 mm. Average width 2.5 mm. Color varies from 2.5GY 5/4 to 2.5GY 6/4.

*Color.*—N 9.5/.

*Number of buds per spur.*—Average 5, varies from 3 to 8.

Flowers:

*Size.*≦Large. Average height 21.2 mm. Average diameter 34.7 mm.

*Petals.*—Number — 5, alternately arranged to sepals. Nearly orbicular, narrows at point of attachment. Outer edge slightly cleft. Average length 16.5 mm. Average width 15.6 mm.

*Sepals.*—Number — 5, alternately arranged to petals. Triangular shape. Both upper and lower surfaces glabrous. Average length 7.3 mm. Average width 4.6 mm. Color — upper surface 2.5GY 5/4, lower surface 2.5GY 6/4.

*Stamens.*—Average number per flower 30. Average filament length 11.8 mm. Filament color N 9.5/. Color of anthers 1.25Y 8/12.

*Pollen.*—Abundant, pollinator required — not self-fruitful. Color — 1.25Y 8/12.

*Pistil.*—Number per flower — usually one. Average length 16.5 mm, stigma is usually at the same height as the anthers. Surface — glabrous. Color — 2.5GY 9/6.

*Fragrance.*—Slight to moderate aroma.

*Blooming period.*—Date of First Bloom Mar. 9, 2002. Date of Petal Fall Mar. 22, 2002. Varies slightly with climatic conditions.

*Color.*—N 9.5/.

*Number flowers per flower bud.*—Average 4, varies from 2 to 4.

*Pedicel.*—Medium length. Average length 26.1 mm. Average width 2.7 mm. Color 2.5GY 8/4.

Fruit:

*Maturity when described.*—Firm ripe.

*Date of first picking.*—May 2, 2002.

*Date of last picking.*—May 9, 2002. Varies slightly with climatic conditions.

*Size.*—Large. Average diameter axially 28.5 mm. Average transversely in suture plane 25.4 mm. Average weight 6.9 grams. Average weight varies slightly with fertility of the soil, amount of fruit set and climatic conditions.

*Form.*—Globose. Slightly flattened at apex and base.
*Suture.*—Shallow, relatively smooth.
*Ventral surface.*—Smooth, nearly rounded.
*Apex.*—Varies from slightly retuse to rounded.
*Base.*—Retuse.
*Cavity.*—Rounded. Average depth 1.8 mm. Average diameter 2.2 mm.

Stem:
*Size.*—Medium. Average length 34.9 mm. Average width 1.6 mm.
*Color.*—Varies from 2.5GY 4/4 to 2.5GY 5/4.

Flesh:
*Ripens.*—Evenly.
*Texture.*—Smooth, relatively meaty.
*Fibers.*—Few, small and tender.
*Firmness.*—Medium firm, comparable to 'Early Burlat' Cherry (non-patented).
*Aroma.*—Slight.
*Amydgalin.*—Undetected.
*Eating quality.*—Good.
*Flavor.*—Very good, good balance between acid and sugar.
*Juice.*—Moderate amount, enhances flavor.
*Brix.*—Average of 13.5°, varies slightly with amount of fruit per tree and climatic conditions.
*Color.*—Varies from 2.5R 4/8 to 5R 3/8. Varies with fruit maturity. Pit cavity color 5R 2/6.

Skin:
*Thickness.*—Medium.
*Surface.*—Smooth.
*Bloom.*—Wanting.
*Tendency to crack.*—None during dry weather, only slight tendency to crack in wet weather, varies with stage of fruit maturity.
*Color.*—Varies from 2.5R 2/4 to 5R 3/10.
*Tenacity.*—Tenacious to flesh.
*Astringency.*—None.

Stone:
*Type.*—Clingstone.
*Size.*—Medium. Average length 11.3 mm. Average width 8.9 mm. Average thickness 7.2 mm.
*Form.*—Ovoid.
*Base.*—Slightly rounded.
*Apex.*—Round to slight apical point.
*Surface.*—Smooth, except for ridges near suture.
*Sides.*—Equal to unequal. Some stones have one side extending further from suture plane.
*Ridges.*—A small, narrow ridge on each side of suture, extending from base to apex.
*Tendency to split.*—None.
*Color.*—Varies from 10YR 7/6 to 10YR 7/8 when dry.

Kernal:
*Form.*—Ovoid.
*Taste.*—Bitter.
*Viability.*—Viable. Good embryo development.
*Size.*—Average length 7.9 mm. Average width 5.1 mm. Average depth 4.4 mm.
*Skin color.*—Varies from 10YR 5/6 to 10YR 6/8 when dry.

Use: Dessert. Market — local and long distance.

Keeping quality: Good. Held well for 21 days in cold storage at 38° to 42° F. and maintained good appearance and eating quality.

Shipping quality: Good. Minimal bruising or scarring in packing and shipping trials.

Plant disease resistance/susceptibility: No specific testing for relative plant/fruit disease has been designed. Under close observation during planting, growing and harvesting of fruit, under normal cultural and growing conditions near Modesto, Calif., no particular plant/fruit disease resistance or susceptibility has been observed. Any variety or selection observed during indexing of plant characteristics with abnormal susceptibility is destroyed and eliminated from our breeding program.

The present new variety of cherry tree, its flowers, foliage and fruit herein described may vary in slight detail due to climate, soil conditions and cultural practices under which the variety may be grown. The present description is that of the variety grown under the ecological conditions prevailing near Modesto, Calif.

It is claimed:

1. A new and distinct variety of cherry tree, substantially as illustrated and described, characterized by its large size, vigorous, upright growth and being a regular and productive bearer of large size fruit with very good flavor and eating quality; the fruit is further characterized by its attractive red skin color and by maturing in the early season with good handling and shipping qualities, and in comparison to 'Early Burlat' Cherry (non-patented), the new variety blooms approximately 7 days earlier and the fruit is approximately 3 days earlier in maturity.

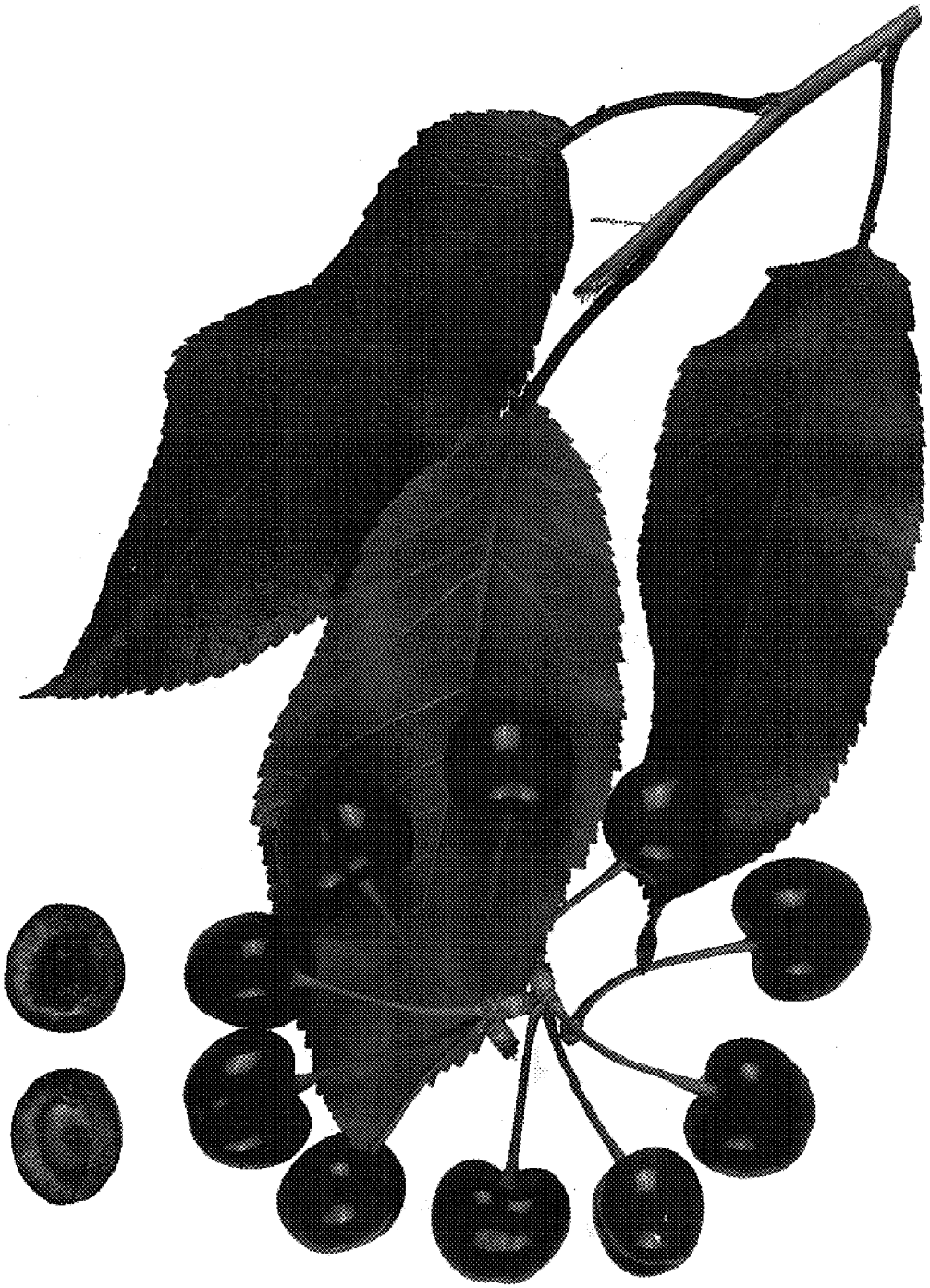

* * * * *